(12) United States Patent
Salo et al.

(10) Patent No.: US 12,279,874 B2
(45) Date of Patent: Apr. 22, 2025

(54) BIO-SIGNAL DETECTION

(71) Applicant: Nokia Technologies Oy, Espoo (FI)

(72) Inventors: Antti Salo, Lohja (FI); Kim Blomqvist, Espoo (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 16/762,867

(22) PCT Filed: Nov. 23, 2018

(86) PCT No.: PCT/EP2018/082394
§ 371 (c)(1),
(2) Date: May 8, 2020

(87) PCT Pub. No.: WO2019/101935
PCT Pub. Date: May 31, 2019

(65) Prior Publication Data
US 2020/0281498 A1 Sep. 10, 2020

(30) Foreign Application Priority Data
Nov. 24, 2017 (EP) ..................................... 17203659

(51) Int. Cl.
*A61B 5/00* (2006.01)
*A61B 5/053* (2021.01)
*A61B 5/308* (2021.01)

(52) U.S. Cl.
CPC .............. *A61B 5/308* (2021.01); *A61B 5/053* (2013.01); *A61B 5/6891* (2013.01); *A61B 5/721* (2013.01);
(Continued)

(58) Field of Classification Search
CPC ............ A61N 1/36034; A61N 1/36114; A61N 1/36146; A61N 1/36157; A61N 1/04;
(Continued)

(56) References Cited

U.S. PATENT DOCUMENTS

| 5,978,693 A | 11/1999 | Hamilton et al. | 600/391 |
| 6,351,665 B1 | 2/2002 | Koch | 600/546 |

(Continued)

FOREIGN PATENT DOCUMENTS

| CN | 101965681 A | 2/2011 |
| EP | 2101408 A1 | 9/2009 |

(Continued)

OTHER PUBLICATIONS

Yang et al., "Motion Artifact Cancellation of Seismocardiographic Recording From Moving Subjects", IEEE Sensors Journal, vol. 16, No. 14, Jul. 15, 2016, pp. 5702-5708.

(Continued)

*Primary Examiner* — Deborah L Malamud
(74) *Attorney, Agent, or Firm* — McCarter & English LLP

(57) ABSTRACT

An apparatus comprising: a first displacement current sensor comprising a first sensing electrode and a first guard electrode, wherein the first displacement current sensor is configured to measure a first sensed signal dependent upon electrical activity of a subjects heart; a second displacement current sensor comprising a second sensing electrode and a second guard electrode, wherein the second displacement current sensor is configured to measure a second sensed signal dependent upon electrical activity of a subjects heart; and circuitry configured to process at least the first sensed signal to compensate for artefacts arising from motion of the subject.

20 Claims, 3 Drawing Sheets

(52) U.S. Cl.
    CPC .............. *A61B 2560/0468* (2013.01); *A61B 2562/0214* (2013.01)

(58) Field of Classification Search
    CPC .... A61N 1/36125; A61N 1/0408; A61N 1/36; A61N 1/36139; A61N 1/36128; A61N 1/3702; A61B 5/1118; A61B 5/486; A61B 5/318; A61B 5/0205; A61B 5/1123; A61B 5/024; A61B 5/4836; A61B 5/7203; A61B 5/7221; A61B 5/7282; A61B 5/375; A61B 5/0006; A61B 5/02; A61B 5/24; A61B 5/25; A61B 5/28; A61B 5/7207; A61B 5/7225; A61B 5/7264; A61B 5/7275
    See application file for complete search history.

(56) References Cited

U.S. PATENT DOCUMENTS

| | | |
|---|---|---|
| 8,753,285 B2 | 6/2014 | Kim et al. |
| 9,011,346 B2 | 4/2015 | Wiard et al. |
| 9,462,956 B2 | 10/2016 | Pandia et al. |
| 2016/0128641 A1 | 5/2016 | Fonseca et al. |
| 2016/0338648 A1 | 11/2016 | Faisal et al. |

FOREIGN PATENT DOCUMENTS

| | | | |
|---|---|---|---|
| EP | 2294979 A1 | 3/2011 | |
| EP | 2101408 B1 * | 5/2012 | ......... A61B 5/04004 |
| EP | 3050501 A1 | 8/2016 | |
| EP | 3488777 A1 | 5/2019 | |
| WO | 2015/018675 A1 | 2/2015 | |
| WO | 2017/012987 A1 | 1/2017 | |

OTHER PUBLICATIONS

Areny et al., "On Bio-Activity Related Signals from Contactless Electrode Measurements", Sensors and Actuators A Physical, vol. 238, Dec. 2015, pp. 1-5.

Jain et al., "Heart Monitoring Systems—A Review", Computers in Biology and Medicine, vol. 54, No. Nov. 1, 2014, pp. 1-13.

Inan et al., "Ballistocardiography and Seismocardiography: A Review of Recent Advances", IEEE Journal of Biomedical and Health Informatics, vol. 19, No. 4 , Jul. 2015, pp. 1414-1427.

Serteyn et al., "Motion Artifacts in Capacitive ECG Measurements: Reducing the Combined Effect of DC Voltages and Capacitance Changes Using an Injection Signal", IEEE Transactions on Biomedical Engineering, vol. 62 , No. 1, Jan. 2015, pp. 264-273.

Peng et al., "A System for Active Compensation of Motion Artifacts in Non-Contact ECG Sensing", IEEE Life Sciences, Feb. 18, 2014, pp. 1-6.

Ueno et al., "Capacitive Sensing of Electrocardiogramatential Through Cloth From the Dorsal Surface of the Body in a Supine Position: A Preliminary Study", IEEE Transactions on Biomedical Engineering, vol. 54 , No. 4 , Apr. 2007, pp. 759-766.

Aleksandrowicz et al., "Wireless and Non-contact ECG Measurement System—the "Aachen SmartChair"", Acta Polytechnica, vol. 47 No. 4-5, 2007, pp. 68-71.

Lim et al., "ECG Measurement on a Chair Without Conductive Contact", IEEE Transactions on Biomedical Engineering, vol. 53, No. 5, May 2006, pp. 956-959.

Lim et al., "ECG Recording on a Bed During Sleep Without Direct Skin-Contact", IEEE Transactions on Biomedical Engineering, vol. 54, No. 4 , Apr. 2007, pp. 718-725.

Prance et al., "Biological and Medical Applications of a New Electric Field Sensor", Proc. ESA Annual Meeting on Electrostatics 2008, Paper N2, Jan. 2008, pp. 1-4.

Prance et al., "Non-Contact Voltage and Electric Field Measurement using the Electric Potential Sensor", Centre for Physical Electronics and Quantum Technology, 2007, 32 pages.

Fukushima et al., "Estimating Heart Rate Using Wrist-Type Photoplethysmography and Acceleration Sensor While Running", 2012 Annual International Conference of the IEEE Engineering in Medicine and Biology Society, Aug. 28-Sep. 1, 2012, pp. 2901-2904.

Sweeney et al., "Artifact Removal in Physiological Signals-Practices and Possibilities", IEEE Transactions on Information Technology in Biomedicine, vol. 16, No. 3, May 2012, pp. 488-500.

Phillips et al., "Evaluation of Electrical and Optical Plethysmography Sensors for Noninvasive Monitoring of Hemoglobin Concentration", Sensors, vol. 12, No. 2, 2012, pp. 1816-1826.

Extended European Search Report received for corresponding European Patent Application No. 17203659.2, dated May 25, 2018, 13 pages.

Serteyn et al., "Using an Injection Signal to Reduce Motion Artifacts in Capacitive ECG Measurements", 35th Annual International Conference of the IEEE EMBS, Jul. 3-7, 2013, pp. 4795-4798.

International Search Report and Written Opinion received for corresponding Patent Cooperation Treaty Application No. PCT/EP2018/082392, dated Feb. 19, 2019, 15 pages.

International Search Report and Written Opinion received for corresponding Patent Cooperation Treaty Application No. PCT/EP2018/082394, dated Feb. 19, 2019, 18 pages.

Office action received for corresponding European Patent Application No. 17203659.2, dated Jun. 16, 2020, 7 pages.

Office action received for corresponding European Patent Application No. 17203659.2, dated Nov. 5, 2020, 5 pages.

Heuer, Stephan, et al., "Motion Artefact Correction for Capacitive ECG Measurement", IEEE, Nov. 2009, pp. 113-116.

\* cited by examiner

BIO-SIGNAL DETECTION

RELATED APPLICATION

This application claims priority to PCT Application No. PCT/EP2018/082394, filed on Nov. 23, 2018, which claims priority to European Application No. 17203659.2, filed on Nov. 24, 2017, each of which is incorporated herein by reference in its entirety.

TECHNOLOGICAL FIELD

Embodiments of the present invention relate to bio-signal detection. In particular, they relate to improving bio-signal detection.

BACKGROUND

Bio-signals are signals that provide information about the functioning of a subject's body. There are a very large number of bio-signals.

Bio-signals that relate to the heart and circulation include, for example, systolic blood pressure, diastolic blood pressure, heart rate, electrocardiogram, pulse wave velocity, phonocardiogram, ballistocardiogram, echocardiogram etc.

Detected bio-signals can suffer from noise arising from many different sources.

It is desirable to remove noise from bio-signals.

BRIEF SUMMARY

According to various, but not necessarily all, embodiments of the invention there is provided an apparatus comprising:

a first displacement current sensor comprising a first sensing electrode and a first guard electrode, wherein the first displacement current sensor is configured to measure a first sensed signal dependent upon electrical activity of a subject's heart;

a second displacement current sensor comprising a second sensing electrode and a second guard electrode, wherein the second displacement current sensor is configured to measure a second sensed signal dependent upon electrical activity of a subject's heart; and circuitry configured to process at least the first sensed signal to compensate for artefacts arising from motion of the subject.

The circuitry may comprise: at least one processor; and at least one memory including computer program code, the at least one memory and the computer program code configured to, with the at least one processor 90, cause the apparatus at least to perform: processing the sensed signal to compensate for artefacts arising from motion of the subject.

According to various, but not necessarily all, embodiments of the invention there is provided examples as claimed in the appended claims.

BRIEF DESCRIPTION

For a better understanding of various examples that are useful for understanding the detailed description, reference will now be made by way of example only to the accompanying drawings in which.

DETAILED DESCRIPTION

Figure 1:
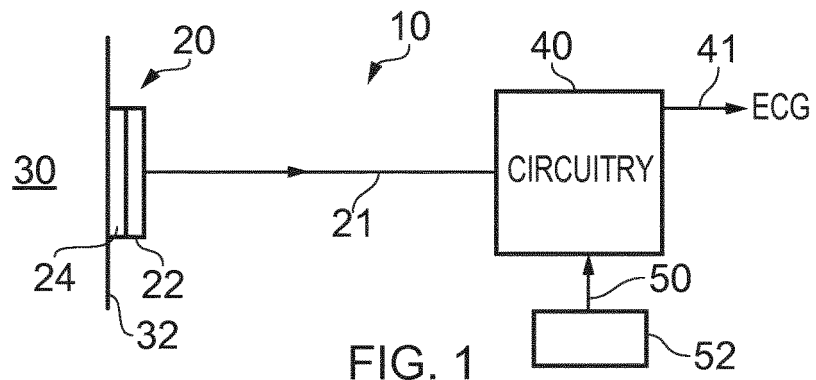
FIG. 1 illustrates an example of an apparatus for processing one or more sensed electrical signals to compensate for artefacts arising from motion of the subject.

FIG. 1 illustrates an example of an apparatus 10 for processing one or more sensed electrical signals 21 dependent upon electrical activity of a subject's heart; to compensate for artefacts arising from motion of the subject. In this way, in some examples, the apparatus 10 obtains an electrocardiogram signal 41 from the one or more sensed electrical signals 21. An electrocardiogram signal 41 is a signal that depends upon the electrical polarization and depolarization of the heart muscles. It is indicative of heart function.

The apparatus 10 may therefore be, or be a part of, a circulation monitoring system or a health monitoring system that uses the electrocardiogram signal 41 to assess heart function. This may find application for patient monitoring, for personal health monitoring, for fitness assessment, for exercise effectiveness monitoring etc.

Figure 2:
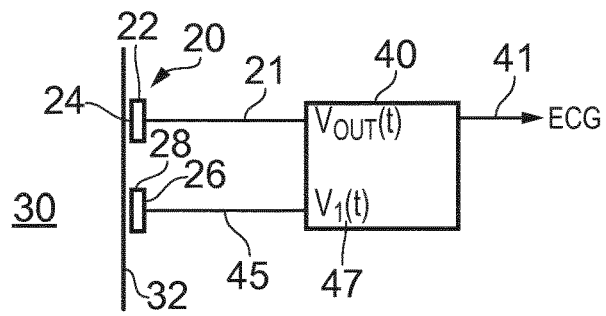
FIGS. 2 and 3 illustrates examples of an apparatus for processing one or more sensed electrical signals to compensate for artefacts arising from motion of the subject.
Figure 3:
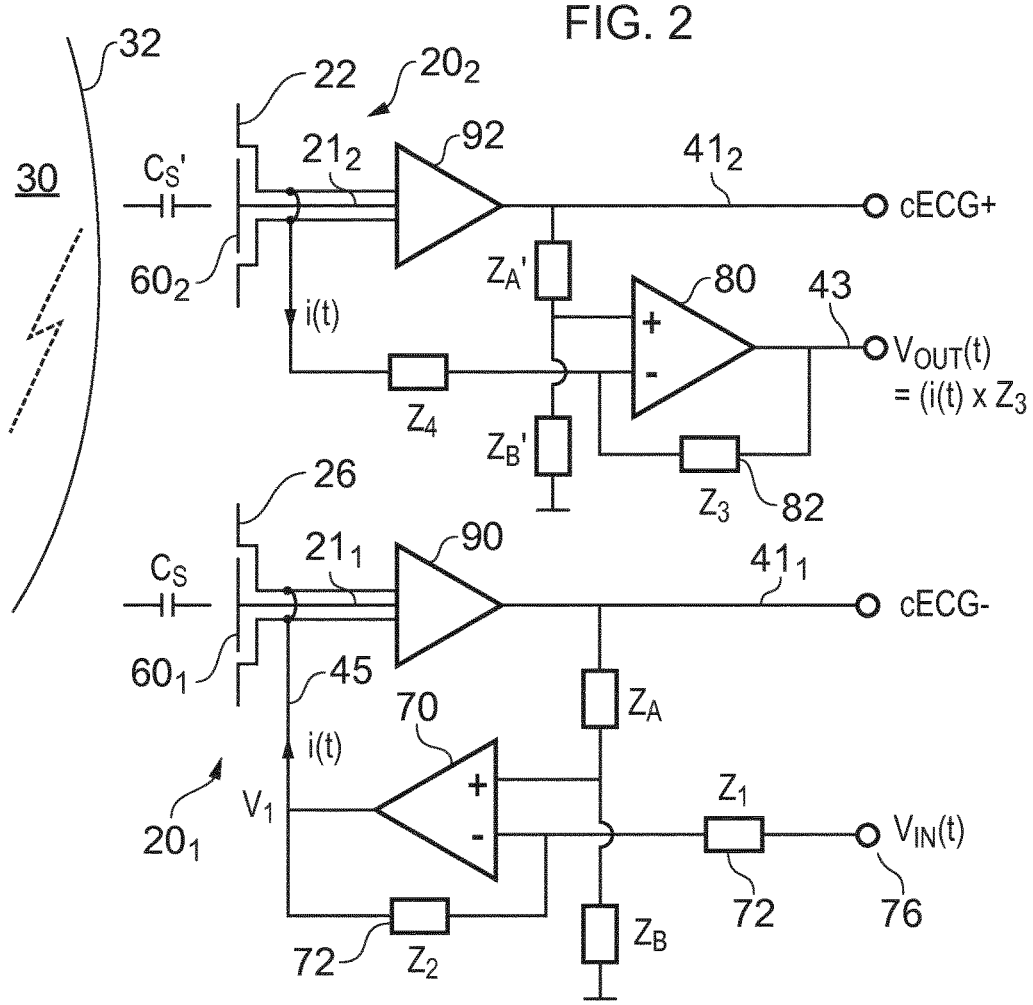

The apparatus 10 comprises at least a displacement current sensor 20 and circuitry 40 operatively connected to the displacement current sensor 20. The connection may, for example, be a direct galvanic connection via a lead, as illustrated in FIGS. 2 and 3.

The displacement current sensor 20 is configured to measure one or more sensed electrical signals 21 dependent upon electrical activity of a heart of a subject 30. The sensor 20 detects the one or more sensed electrical signals 21. The sensor 20 may or may not further process the detected electrical signal to produce the one or more sensed electrical signals 21. Measurement does not therefore imply that the one or more sensed electrical signals is quantised, although it may be.

The total current density (defined by curl H) has a galvanic component J and a displacement component dD/dt, where D=εE. The displacement current sensor 20 measures a value dependent upon D and its variation over time, dD/dt.

The displacement current sensor 20 comprises at least one electrode 22 in proximity to the skin 32 of the subject 30 but electrically insulated therefrom.

In some examples the displacement current sensor 20 comprises electrical insulation 24 for insulating the at least one electrode 22 from the subject's skin 32.

In some examples, material between the electrode 22 and the subject's skin 30 additionally or alternatively provides electrical insulation of the electrode 22 from the subject's skin 32.

The electrical insulation prevents the displacement current sensor 20 from receiving the galvanic component J of the total current density.

The circuitry 40 is configured to process the one or more sensed electrical signals 21 to compensate for artefacts arising from motion of the subject. The compensation for motion artefacts removes noise from the sensed electrical signal 21 producing a version of the electrical signal 21 that is less affected by noise.

The circuity 40 receives a motion associated signal 50 that is associated with motion of the electrode 22 of the displacement current sensor 20 relative to the user 30.

For example, the motion associated signal 50 may be a motion dependent signal that is dependent upon or responsive to motion of the electrode 22 of the displacement current sensor 20 relative to the user 30. Additionally or alternatively, the motion associated signal 50 may be a force dependent signal that is dependent upon or responsive to force that causes motion of the electrode 22 of the displacement current sensor 20 relative to the user 30.

In some examples, the apparatus 10 comprises one or more motion-associated sensors 52 for producing one or more motion associated signals 50.

For example, a motion-associated sensor 52 may be a motion sensor, a distance sensor; a force sensor, a pressure sensor, a deformation sensor and/or a body wearable motion sensor.

The motion-associated sensor 52 may, for example, be a capacitive sensor, a radio frequency sensor, an ultrasound sensor, an optical sensor; and electromagnetic film sensor, a piezoelectric sensor, a strain gauge sensor, an accelerometer, a gyroscope, and/or a magnetometer.

The circuitry 40 may be any suitable circuitry. It may be an arrangement of discrete components, and/or may comprise programmable gate arrays, and/or may comprise programmed processors, for example.

In some but not necessarily all examples, the circuitry 40 is configured to measure a variable capacitance caused by motion of the electrode 22 of the displacement current sensor 20 relative to the user 30. The circuitry 40 may be configured to measure a variable reactance caused by motion of the electrode 22 of the displacement current sensor 20 relative to the user 30 by measuring, in the Imaginary domain, modulation of a reference signal by the variable reactance. In the examples illustrated in FIGS. 2 and 3, the reference signal is an external signal 45 applied to the subject 30.

In the examples of FIGS. 2 and 3, the circuitry 40 is configured to process the one or more sensed electrical signals 21 to obtain a noise-reduced electrocardiogram signal 41. The circuitry 40 measures the artefacts caused by motion as a modulation of the electrical reference signal 45 provided to the subject 30 via the first electrode 26 by the circuitry 40. The circuitry 40 is configured to process the sensed signal 21 to compensate for the artefacts arising from motion of the subject.

The circuitry 40 is configured to apply a time-variable voltage V1, as the reference signal 45, to a first electrode 26, for example via a first operational amplifier, and measure a time-variable signal $V_{out}$, for example at an output of a second operational amplifier.

In these examples, the first electrode 26 is in proximity to the skin 32 of the subject 30 but electrically insulated therefrom. In some examples, electrical insulation 24 insulates the electrode 26 from the subject's skin 32. In some examples material between the electrode 26 and the subject's skin 30 additionally or alternatively provides electrical insulation of the electrode 26 from the subject's skin 32.

The electrical reference signal 45 has one or more high frequency components, for example, greater than 1 kHz. For example, the electrical reference signal 45 may have a significant component over 100 kHz, for example in the range 100-500 kHz, or in some embodiments may lie entirely within the range over 100 kHz or 100-500 kHz. The electrical reference signal 45 may, for example, be a pure tone (single frequency).

In the example of FIG. 3, a first displacement current sensor $20_1$ comprises a first ECG electrode $60_1$ for measuring a first ECG signal $41_1$, and a first electrode 26 for injection of a current (reference signal 45), and a second displacement current sensor $20_2$ comprises a second ECG electrode $60_2$ for measuring a second ECG signal $41_2$, and a second electrode 22 for measuring motion artefacts. The first displacement current sensor $20_1$ and the second displacement current sensor $20_2$ are physically distinct and separate.

The circuitry 40 is configured to apply a time-variable voltage $V_1$ to a first electrode 26 via a first operational amplifier 70, and provide a time-variable signal 43 (voltage $V_{out}$) at an output of a second operational amplifier 80.

Figure 4A:
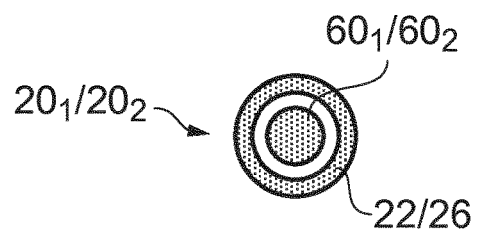
FIG. 4 illustrates an example of a configuration of a guard electrode and an ECG electrode.

As illustrated in more detail in FIG. 4, the first electrode 26 and the second electrode 22 are guard electrodes for the respective first and second ECG electrodes $60_1$, $60_2$. Consequently, the first displacement current sensor $20_1$ comprises a sensing electrode $60_1$ and also at least one guard portion, the guard electrode 26. Consequently, the second displacement current sensor $20_2$ comprises a sensing electrode $60_2$ and also at least one guard portion, the guard electrode 22.

The ECG electrode is centrally located. In these examples it is circular but this is not necessarily essential. The electrode 26/22 is separated from the ECG electrode $60_1$/$60_2$, in this example, low relative permittivity gaps are used for separation.

The electrode 26/22 is a circle circumscribing but separated from the ECG electrode $60_1$/$60_2$.

Returning to FIG. 3, the ECG signal $41_1$ received at the ECG electrode $60_1$ is applied, via op-amp 90, as a virtual earth at a +ve terminal of a first op-amp 70. A voltage divider may be used in some examples. For example, impedances $Z_A$ and $Z_B$ may be connected in series between the output of the op-amp 90 and ground, and an intermediate node between impedances $Z_A$ and $Z_B$ may be connected to +ve terminal of the first op-amp 70.

The ECG signal $41_2$ received at the ECG electrode $60_2$ is applied, via op-amp 92, as a virtual earth at a +ve terminal of a second op-amp 80. A voltage divider may be used in some examples. For example, impedances $Z_A'$ and $Z_B'$ may be connected in series between the output of the op-amp 92 and ground, and an intermediate node between impedances $Z_A'$ and $Z_B'$ may be connected to the +ve terminal of the second op-amp 80.

The first op-amp 70 generates at its output a current and a voltage $V_1$ at the first guard electrode 26. The first op-amp 70 is arranged for closed loop negative feedback via an impedance 72 connected between its output and its −ve terminal. The impedance 72 has a value $Z_2$. The first op-amp 70 is arranged to receive an input at its −ve terminal, via an impedance 74, from a variable voltage source 76. The variable voltage source 76 produces voltage $V_{in}(t)$. The impedance 74 has a value $Z_1$. The first ECG signal $41_1$ received at the first ECG electrode $60_1$ is applied, after amplification by op-amp 90, as a virtual earth at the +ve terminal of the first op-amp 70.

The second op-amp 80 receives at a −ve terminal a voltage from the second guard electrode 22. The second op-amp 80 is arranged for closed loop negative feedback via an impedance 82 connected between its output and its −ve terminal. The impedance 82 has a value $Z_3$. The second ECG signal $41_2$ received at the second ECG electrode $60_2$ is applied, after amplification by op-amp 92, as a virtual earth at the +ve terminal of the second op-amp 80. The second op-amp 80 generates at its output a voltage $V_{out}$ which is the motion artefact signal 43. In some examples, an impedance $Z_4$ may be connected between the second guard electrode 22 and the –ve terminal of the second op-amp 80.

The current at the –ve terminal of the second op-amp 80 depends on the voltage ($V_1$) at the first electrode 26 (relative to virtual earth) and an unknown impedance Z associated with the current path between the electrodes 22, 26 and through the subject's body. The impedance Z is comprised of a steady state value and a variable value that may be assumed to arise substantially from relative motion between the electrodes 22, 26 and the subject's body. The output of the op-amp 80 is therefore a variable impedance signal 43 caused by relative motion.

The current at the –ve terminal of the first op-amp 70 is $V_{in}/Z_1$, where $V_{in}$ is the variable voltage (relative to virtual earth) applied to a –ve input of the first op-amp 70 via impedance $Z_1$. The first op-amp 70 is arranged for closed loop, negative feedback. The output of the first op-amp 70 is therefore $V_1=V_{in}*(1+Z_2/Z_1)$. The current at the –ve terminal of the second op-amp 80 is $V_1/Z$ where $V_1$ is the variable voltage (relative to virtual earth) applied to a –ve input of the second op-amp 80 via the inter-electrode impedance Z. The second op-amp 80 is arranged for closed loop, negative feedback. The output of the second op-amp 80 is therefore $V_{out}=Z_3*V_1/Z=V_{in}*(Z_3/Z)*(1+Z_2/Z_1)$.

It is possible to separate the part of $V_{out}$ that arises as a consequence of variation in Z from the part of $V_{out}$ that arises as a consequence of variation in $V_{in}$.

This may, for example, be achieved by removing $V_{in}$ from $V_{out}$ in the frequency domain using a demodulator.

If $Z_1$, $Z_2$, $Z_3$ are resistors, then at the higher frequencies of $V_{in}$ the steady state impedance of the body may be considered to be primarily resistive. The changing impedance arising from the distance between the electrodes 22/26 and the skin surface will be primarily reactive (capacitive).

Changes in the imaginary (reactive) part of the variable impedance signal 43 may therefore be attributed to variation in capacitance arising from the relative motion of the electrodes 22,26 and the body. These represent motion artefacts in the sensed signal 21.

Figure 5:
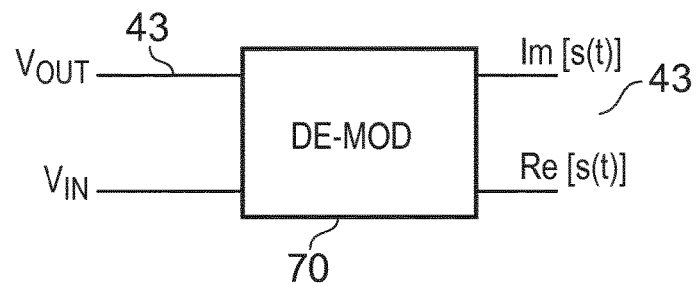
FIG. 5 illustrates an example of a demodulation circuit.

FIG. 5 illustrates an example of a demodulation circuit. The demodulation circuit processes the input time-variable voltage $V_{in}$ and the output time-variable voltage $V_{out}$ to obtain Imaginary and Real components of the variable impedance signal 43.

The demodulation circuit may be configured to calculate how the complex transfer function between the input time-variable voltage $V_{in}$ and the output time-variable voltage $V_{out}$ varies over time.

The apparatus 10 therefore comprises: a first displacement current sensor $20_1$ comprising a first sensing electrode $60_1$ and a first guard electrode 26 and a second displacement current sensor $20_2$ comprising a second sensing electrode $60_2$ and a second guard electrode 22. The first displacement current sensor $20_1$ is configured to measure a first sensed signal $21_1$ dependent upon electrical activity of a subject's heart. The second displacement current sensor $20_2$ is configured to measure a second sensed signal $21_2$ dependent upon electrical activity of a subject's heart.

The first displacement current sensor $20_1$ comprises electrical insulation for insulating the first sensing electrode $60_1$ from the subject's skin. The second displacement current sensor $20_2$ comprises electrical insulation for insulating the second sensing electrode $60_2$ from the subject's skin.

The first displacement current sensor $20_1$ and the second displacement current sensor $20_2$ are separated in space by at least several centimeters (more than 2 or 3 cm). The first displacement current sensor $20_1$ is movable relative to the subject and is not affixed to the subject. The second displacement current sensor $20_2$ is movable relative to the subject and the first displacement current sensor $20_1$, and is not affixed to the subject. The first displacement current sensor $20_1$ and the second displacement current sensor $20_2$ can be embedded in a bed or other furniture.

The apparatus 10 comprises circuitry configured to process the first sensed signal $21_1$ to compensate for artefacts arising from motion of the subject and to process the second sensed signal $21_2$ to compensate for artefacts arising from motion of the subject.

The circuitry is configured to apply a reference signal 45 to one of the first guard electrode 26 and the second guard electrode 22 and to sense at the other of the first guard electrode 26 and the second guard electrode 22 an additional signal dependent upon motion of the subject and to use the additional signal to estimate artefacts arising from motion of the subject and compensate the first sensed signal and/or the second sensed signal. In the illustrated example, the circuitry is configured to apply a reference signal 45 to the first guard electrode 26 and to sense at the second guard electrode 22 an additional signal dependent upon motion of the subject. The reference signal 45 is a first time-variable voltage and the additional signal is a second time-variable voltage dependent upon the first time-variable voltage and motion of the subject. In this example, the reference signal 45 is continuously applied and the additional signal is sensed continuously and contemporaneously.

The first sensed signal and the second sensed signal are used, as virtual earth, for applying the reference signal 45 and for sensing the additional signal. The circuitry is configured to apply the first time-variable voltage $V_1$ to the first guard electrode 26 via an operational amplifier 70, measure a second time-variable voltage $V_{out}$ at an output of another operational amplifier 80. An input to the operational amplifier 80 is connected to the second guard electrode 22. An impedance $Z_3$ is connected between the input and the output of the operational amplifier 80. At least a part of the impedance between the first and second guard electrodes 26, 22 is measured using at least the first time-variable voltage and the second time-variable voltage to estimate motion of the subject.

The operational amplifier 80 is virtually earthed by an ECG signal received at the second sensing electrode $60_2$ adjacent the second guard electrode 22 and guarded by the second guard electrode and the operational amplifier 70 is virtually earthed by an ECG signal received at the first sensing electrode $60_1$ adjacent the first guard electrode 26 and guarded by the first guard electrode 26. The apparatus 10 may be configured to use at least a part of the impedance between the first and second guard electrodes as an external reference signal for an adaptive filter for filtering the first sensed signal and/or the first sensed signal.

The circuitry is thus configured to process the first sensed signal to compensate for artefacts arising from motion of the subject, to provide an ECG signal. The circuitry is configured to process the second sensed signal to compensate for artefacts arising from motion of the subject, to provide an ECG signal.

It will be appreciated than in the apparatus 10, the sensed signal 21 is used, as a virtual earth, to compensate for artefacts arising from motion of the subject. The sensed signal 21 is used, as virtual earth, for sensing variations, compared to an applied reference signal 45, used to compensate for artefacts arising from motion of the subject. A first displacement current sensor $20_1$ is configured to apply the reference signal 45, using a first sensed signal as virtual earth. A second displacement current sensor $20_2$ is configured to sense the additional signal using a second sensed signal as virtual earth. The first displacement current sensor $20_1$ is configured to apply the reference signal 45 via first guard electrode 26 and sense the first sensed signal using an adjacent first sensing electrode $60_1$, guarded by the first guard electrode 26. The second displacement current sensor $20_2$ is configured to sense the additional signal via a second guard electrode 22 and sense the second sensed signal using an adjacent second sensing electrode $60_2$, guarded by the second guard electrode 22.

Figure 6A:
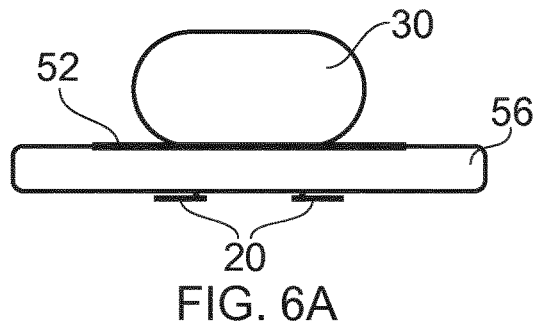
FIGS. 6A, 6B, 6C illustrate examples of motion-associated sensors which may, optionally, be fixed to articles.
Figure 6B:
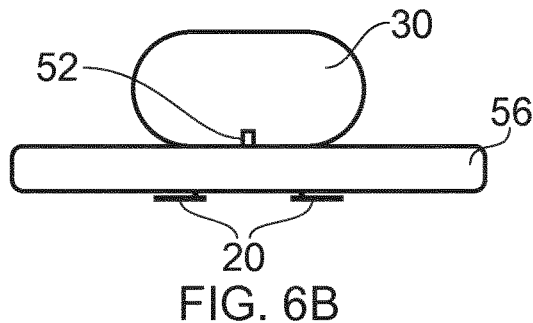
Figure 6C:
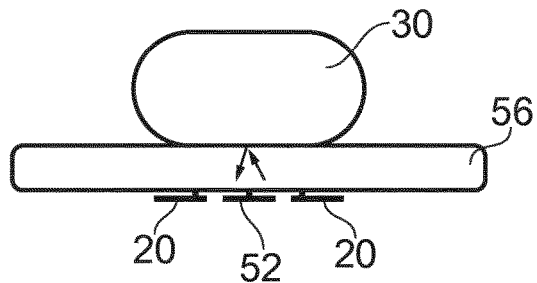

FIGS. 6A, 6B, 6C illustrate examples of motion-associated sensors 52 configured to provide one or more motion associated signals 50. A motion-associated sensor 52 produces a motion associated signal 50 that is associated with motion of the electrode 22 of the displacement current sensor 20 relative to the user 30.

For example, as illustrated in FIG. 6A, the motion associated signal 50 may be a force dependent signal that is dependent upon or responsive to a force that causes motion of the electrode 22 of the displacement current sensor 20 relative to the user 30. The motion-associated sensor 52 may, for example, be a force sensor, a pressure sensor, and/or a deformation sensor. The motion-associated sensor 52 may, for example, be an electromagnetic film sensor, a piezoelectric sensor, a strain gauge sensor.

For example, as illustrated in FIG. 6B, the motion associated signal 50 may be a motion dependent signal that is dependent upon or responsive to motion of the subject's body (e.g. relative to a fixed electrode 22 of the displacement current sensor 20). The motion-associated sensor 52 may, for example, be a body wearable motion sensor. The motion-associated sensor 52 may, for example, be an accelerometer, a gyroscope, and/or a magnetometer.

For example, as illustrated in FIG. 6C, the motion associated signal 50 may be a motion dependent signal that is dependent upon or responsive to motion of the electrode 22 of the displacement current sensor 20 relative to the user 30. The motion-associated sensor 52 may, for example, be a motion sensor or a distance sensor. The motion-associated sensor 52 may, for example, be a capacitive sensor, a radio frequency sensor, an ultrasound sensor, an optical sensor.

The circuitry 40 illustrated in FIG. 3, produces the variable impedance signal 43 as a motion associated signal 50. The variable impedance signal 43 varies with the varying capacitance between ECG electrode $60_1$ and the subject's body and ECG electrode $60_2$ and the subject's body.

The motion-associated sensors 52 may be part of the apparatus 10 or separate to the apparatus 10.

The motion-associated sensor 52 may perform one of more of the sensing functions described with reference to FIGS. 6A to 6C.

In the example of FIGS. 6A to 6C, the displacement current sensor 20 is movable relative to the subject and is not affixed to the subject. For example, the electrode 22 (26) of a displacement current sensor 20 is movable relative to the subject and is not affixed to the subject.

In these examples, but not necessarily all examples, the displacement current sensor 20 is fixed to an article 56 adjacent the subject 30. The article 56 may, for example, be a bed or other furniture.

FIGS. 7A to 7D illustrate further examples of circuitry 40 configured to process the one or more sensed electrical signals 21 to compensate for artefacts arising from motion of the subject. The compensation for motion artefacts removes noise from the sensed electrical signal 21 producing an electrical signal 21 less affected by noise.

Figure 7A:
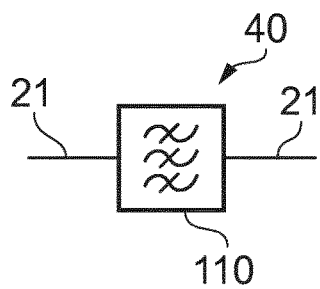
FIGS. 7A to 7D illustrate further examples of circuitry configured to process the one or more sensed electrical signals to compensate for artefacts arising from motion of the subject.

In the example of FIG. 7A, the circuitry 40 is configured to process the sensed signal 21 to compensate for artefacts arising from motion of the subject by passing the sensed signal 21 through a band pass filter 110 configured to filter the sensed signal 21 to compensate for artefacts arising from motion of the subject 30. It may be desirable for the filter 110 to be adaptive and adapt in response to the motion associated signal 50. In some but not necessarily all examples, the filter 110 may have a fixed bandwidth or an adaptive bandwidth in the range 1-40 kHz.

Figure 7B:
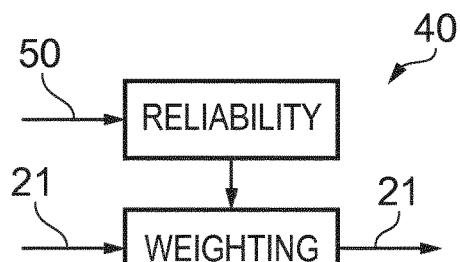

In the example of FIG. 7B, the circuitry 40 is configured to process the sensed signal 21 to compensate for artefacts arising from motion of the subject by:
i) determining a reliability of the sensed signal 21 over time based on the motion associated signal 50. For example, if the motion associated signal 50 indicates motion for a first period of time, then the sensed signal 21 may be flagged as unreliable for that first period of time. If the motion associated signal 50 indicates no motion for a second period of time, then the sensed signal 21 may be flagged as reliable for that second period of time.
ii) processing the sensed signal 21 using weightings based on the determined reliability. For example, if the sensed signal 21 is flagged as reliable it may have a weighting of 1 (multiplication factor=1) and if the sensed signal 21 is flagged as unreliable it may have a weighting of 0 (multiplication factor=0). It is of course possible to have weightings between 0 and 1 depending upon the degree of reliability/unreliability.

Figure 7C:
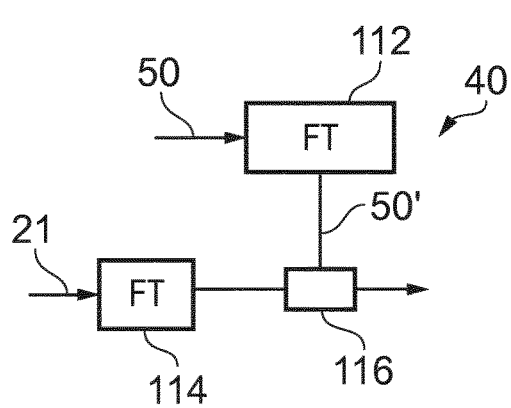

In the example of FIG. 7C, the circuitry 40 is configured to process the sensed signal 21 to compensate for artefacts arising from motion of the subject by:
measuring artefacts arising from motion of the subject; and
in the frequency domain, removing the measured artefacts from the sensed signal.

The motion associated signal 50 may be used to represent artefacts arising from motion of the subject 30. The motion associated signal 50 may be converted 112 to the frequency domain by, for example, using a transform function such as a Fourier Transform (FT). The sensed signal 21 may be converted 112 to the frequency domain by, for example, using a transform function such as a Fourier Transform (FT).

A processor 116 may be used to remove the measured artefacts from the sensed signal in the frequency domain.

For example, it may be determined that the spectral components 50' of the motion associated signal 50 represent noise in the spectral components of the sensed signal 21. The spectral components of the sensed signal that correspond to the spectral components of the motion associated signal 50 may be adapted to remove motion artefacts. In some examples they may be reduced. In some examples, they may be removed.

Figure 7D:
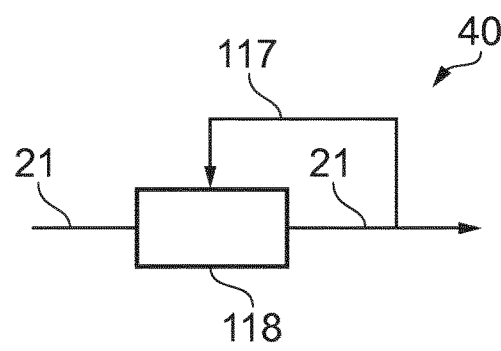

In the example of FIG. 7D, the circuitry 40 is configured to process the sensed signal 21 to compensate for artefacts arising from motion of the subject by using an adaptive filter 118 for filtering the sensed signal 21. The filtered signal or some other reference signal is used for updating the adaptive filter 118. For example, at least a part of the impedance between the first and second electrodes $60_1$, $60_2$ may be used as an external reference signal 117 for the adaptive filter 118 for filtering the sensed signal 21. In some but not necessarily all examples, the filter 118 may have an adaptive bandwidth in the range 1-40 kHz.

Implementation of the circuitry 40 may be as a controller 96, for example. The controller 96 may be implemented in hardware alone, have certain aspects in software including firmware alone or can be a combination of hardware and software (including firmware).

Figure 8:
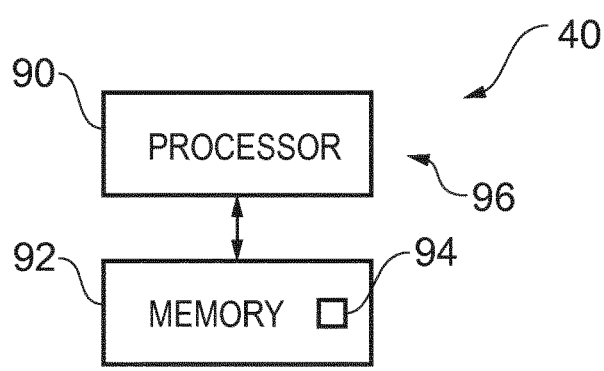
FIG. 8 illustrates an example of a controller configured to process the one or more sensed electrical signals to compensate for artefacts arising from motion of the subject.

As illustrated in FIG. 8 the controller 96 may be implemented using instructions that enable hardware functionality, for example, by using executable instructions of a computer program 94 in a general-purpose or special-purpose processor 90 that may be stored on a computer readable storage medium (disk, memory etc) to be executed by such a processor 90.

The processor 90 is configured to read from and write to the memory 92. The processor 90 may also comprise an output interface via which data and/or commands are output by the processor 90 and an input interface via which data and/or commands are input to the processor 90.

The memory 92 stores a computer program 94 comprising computer program instructions (computer program code) that controls the operation of the apparatus 10 when loaded into the processor 90. The computer program instructions, of the computer program 94, provide the logic and routines that enables the apparatus to perform the methods illustrated in FIG. 11. The processor 90 by reading the memory 92 is able to load and execute the computer program 94.

The apparatus 10 therefore comprises:
at least one processor 90; and
at least one memory 92 including computer program code
the at least one memory 92 and the computer program code configured to, with the at least one processor 90, cause the apparatus 10 at least to perform:
measuring a sensed signal, from a displacement current sensor 20, dependent upon electrical activity of a subject's heart; and
processing the sensed signal 21 to compensate for artefacts arising from motion of the subject 30.

The computer program 94 may arrive at the apparatus 10 via any suitable delivery mechanism. The delivery mechanism may be, for example, a non-transitory computer-readable storage medium, a computer program product, a memory device, a record medium such as a compact disc read-only memory (CD-ROM) or digital versatile disc (DVD), an article of manufacture that tangibly embodies the computer program 94. The delivery mechanism may be a signal configured to reliably transfer the computer program 94. The apparatus 10 may propagate or transmit the computer program 94 as a computer data signal.

Although the memory 92 is illustrated as a single component/circuitry it may be implemented as one or more separate components/circuitry some or all of which may be integrated/removable and/or may provide permanent/semi-permanent/dynamic/cached storage.

Although the processor 90 is illustrated as a single component/circuitry it may be implemented as one or more separate components/circuitry some or all of which may be integrated/removable. The processor 90 may be a single core or multi-core processor.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' refers to all of the following:
(a) hardware-only circuit implementations (such as implementations in only analog and/or digital circuitry) and
(b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions and
(c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

Figure 9:
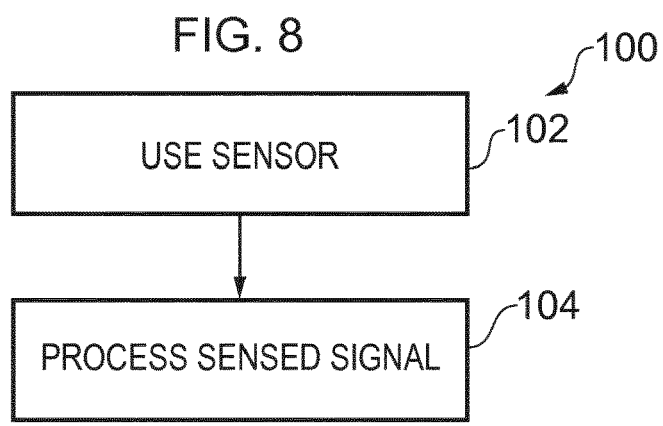
FIG. 9 illustrates an example of a method.

FIG. 9 illustrates an example of a method 100 comprising:
at block 102, using a displacement current sensor 20 to measure a sensed signal 21 dependent upon electrical activity of a subject's heart;
at block 104, processing the sensed signal 21 to compensate for artefacts arising from motion of the subject 30.

The method, when applied to the apparatus illustrated in FIG. 3, comprises, at block 102, using a first displacement current sensor, comprising a first sensing electrode and a first guard electrode, to measure a first sensed signal dependent upon electrical activity of a subject's heart and using a second displacement current sensor, comprising a second sensing electrode and a second guard electrode, to measure a second sensed signal dependent upon electrical activity of a subject's heart; and, at block 104, processing the first sensed signal to compensate for artefacts arising from motion of the subject and/or processing the second sensed signal to compensate for artefacts arising from motion of the subject.

The blocks illustrated in the FIG. 9 may represent steps in a method and/or sections of code in the computer program 94. The illustration of a particular order to the blocks does not necessarily imply that there is a required or preferred order for the blocks and the order and arrangement of the block may be varied. Furthermore, it may be possible for some blocks to be omitted.

Where a structural feature has been described, it may be replaced by means for performing one or more of the functions of the structural feature whether that function or those functions are explicitly or implicitly described.

As used here 'module' refers to a unit or apparatus that excludes certain parts/components that would be added by an end manufacturer or a user. The apparatus 10 may be a module.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
at least one processor; and
at least one memory storing instructions, that when executed by the at least one processor, cause the apparatus to at least:
inject a first time-variable voltage via a first operational amplifier as a current reference signal using a positive virtual earth terminal of a first displacement current sensor comprising a first sensing electrode and a first guard electrode,
wherein the first sensing electrode is configured to measure a first sensed signal dependent upon electrical activity of a subject's heart,
wherein the first operational amplifier generates at its output to a second operational amplifier a current and a voltage at the first guard electrode,
wherein the second operational amplifier receives at a negative virtual earth terminal a voltage from a second guard electrode of a second displacement current sensor,
wherein the second operational amplifier generates at its output a voltage which is a motion artefact signal arising from motion of the subject's heart; and
apply a second time-variable voltage to an output of a second sensing electrode;
measure artefacts arising from motion of the subject, and in a frequency domain, remove the measured artefacts from the first sensed signal or second sensed signal,
wherein the removing comprises removing the first time-variable voltage from the second time-variable voltage output of the second sensing electrode in the frequency domain;
measure the first sensed signal or the second sensed signal dependent upon electrical activity of a subject's heart with the second sensing electrode and the second guard electrode of the second displacement current sensor;
apply the current reference signal to the first guard electrode and to sense at the second guard electrode an additional signal based on the second time-variable voltage and dependent upon the first time-variable voltage,
measure at least a part of variable impedance signal caused by relative motion impedance between the first guard electrode and the second guard electrode using at least the first time-variable voltage and the second time-variable voltage to identify a motion of the subject; and
process at least the first sensed signal or the second sensed signal as a virtual applying the additional signal to compensate for the motion artefact signal for removing noise from the variable impedance signal and producing an electrical signal less affected by noise.

2. An apparatus as claimed in claim 1, wherein the at least one non-transitory memory is storing instructions executed by the at least one processor to cause the apparatus to sense at the second guard electrode, using one of the first operational amplifier or the second operational amplifier arranged for closed loop negative feedback via an impedance connected between an output of one of the first operational amplifier or the second operational amplifier and the negative virtual earth terminal of one of the first operational amplifier or the second operational amplifier.

3. An apparatus as claimed in claim 2, wherein the at least one non-transitory memory is storing instructions executed by the at least one processor to cause the apparatus to apply a voltage dependent upon the second sensed signal to the positive virtual earth terminal of the first operational amplifier or a positive virtual earth terminal of the second operational amplifier.

4. An apparatus as claimed in claim 1, wherein the first displacement current sensor and the second displacement current sensor are separated in space by at least several centimeters.

5. An apparatus as claimed in claim 1, wherein the current reference signal is the first time-variable voltage and the additional signal is the second time-variable voltage dependent upon the first time-variable voltage and motion of the subject.

6. An apparatus as claimed in claim 1, wherein the first sensed signal and the second sensed signal are used, as virtual earth, for applying the reference signal and for sensing the additional signal.

7. An apparatus as claimed in claim 1, wherein the first displacement current sensor comprises electrical insulation for insulating the first sensing electrode from the subject's skin and wherein the second displacement current sensor comprises electrical insulation for insulating the second sensing electrode and the second guard electrode from the subject's skin.

8. An apparatus as claimed in claim 7, wherein the first displacement current sensor is movable relative to the subject and is not affixed to the subject and wherein the second displacement current sensor is movable relative to the subject and the first displacement current sensor, and is not affixed to the subject.

9. An apparatus as claimed in claim 8, wherein the first displacement current sensor and the second displacement current sensor are embedded in a bed or other furniture.

10. An apparatus as claimed in claim 1, wherein the at least one non-transitory memory is storing instructions executed by the at least one processor to cause the apparatus to process the first sensed signal or the second sensed signal to compensate for artefacts arising from motion of the subject, to provide an electrocardiogram signal.

11. An apparatus as claimed in claim 1, wherein the at least one non-transitory memory is storing instructions executed by the at least one processor to cause the apparatus to process the first sensed signal to compensate for artefacts arising from motion of the subject comprises: a band pass filter for filtering the first sensed signal or the second sensed signal to compensate for artefacts arising from motion of the subject.

12. An apparatus as claimed in claim 1, wherein the at least one non-transitory memory is storing instructions executed by the at least one processor to cause the apparatus to process the first sensed signal to compensate for artefacts arising from motion of the subject is configured to: determine reliability of the first sensed signal or second sensed signal over time based on motion of the subject, and process the first sensed signal or second sensed signal using weightings based on the determined reliability.

13. An apparatus as claimed in claim 1, wherein based on the first time-variable voltage being a higher frequency in a steady state, impedance of the subject it is considered to be primarily resistive.

14. An apparatus as claimed in claim 1, wherein the at least one non-transitory memory is storing instructions executed by the at least one processor to cause the apparatus to compensate for artefacts arising from motion of the subject comprises: an adaptive filter for filtering the first sensed signal or second sensed signal.

15. An apparatus as claimed in claim 1, wherein the at least one non-transitory memory is storing instructions executed by the at least one processor to cause the apparatus to compensate for artefacts arising from motion of the subject is configured to apply the first time-variable voltage to the first guard electrode via the first operational amplifier, measure the second time-variable voltage at an output of a second operational amplifier wherein an input to the second operational amplifier is connected to the second guard electrode, an impedance being connected between the input and the output of the second operational amplifier, wherein at least a part of the impedance between the first and second guard electrodes is estimated using at least the first time-variable voltage and the second time-variable voltage to estimate motion of the subject.

16. An apparatus as claimed in claim 15, wherein the first operational amplifier is virtually earthed by an electrocardiogram signal received at the first sensing electrode adjacent the first guard electrode and guarded by the first guard electrode and the second operational amplifier is virtually earthed by an electrocardiogram signal received at the second sensing electrode adjacent the second guard electrode and guarded by the second guard electrode.

17. An apparatus as claimed in claim 15, configured to use at least a part of the impedance between the first and second guard electrodes as an external reference signal for an adaptive filter for filtering at least the first sensed signal.

18. An apparatus as claimed in claim 1, configured as part of a circulation monitoring system or a health monitoring system that assesses heart function.

19. A method comprising:
using a first displacement current sensor, comprising a first sensing electrode and a first guard electrode for injection of a first time-variable voltage via a first operational amplifier as a current reference signal,
wherein the first sensing electrode is configured to measure a first sensed signal dependent upon electrical activity of a subject's heart, and
apply a second time-variable voltage to an output of a second sensing electrode;
measure artefacts arising from motion of the subject, and in a frequency domain,
remove the measured artefacts from the first sensed signal or second sensed signal,
wherein the removing comprises removing the first time-variable voltage from the second time-variable voltage output of the second sensing electrode in the frequency domain;
using a second displacement current sensor, comprising a second sensing electrode and a second guard electrode, wherein the second sensing electrode is configured to measure the first sensed signal or the second sensed signal dependent upon electrical activity of a subject's heart,
wherein the first operational amplifier generates at its output to a second operational amplifier a current and a voltage at the first guard electrode,
wherein the second operational amplifier receives at a negative virtual earth terminal a voltage from the second guard electrode of a second displacement current sensor,
wherein the second operational amplifier generates at its output a voltage which is a motion artefact signal arising from motion of the subject's heart;
applying the current reference signal to the first guard electrode;
sensing at the second guard electrode an additional signal based on the second time-variable voltage and dependent upon the first time-variable voltage;
measuring at least a part of variable impedance signal caused by relative motion impedance between the first guard electrode and the second guard electrode using at least the first time-variable voltage and the second time-variable voltage to identify a motion of the subject; and
processing at least the first sensed signal or the second sensed signal applying the additional signal to compensate for the motion artefact signal for removing noise from the variable impedance signal and producing an electrical signal less affected by noise.

20. A non-transitory computer readable medium comprising program instructions stored thereon for performing at least the following:
using a first displacement current sensor, comprising a first sensing electrode and a first guard electrode for injection of a first time-variable voltage via a first operational amplifier as a current reference signal, wherein the first sensing electrode is configured to measure a first sensed signal dependent upon electrical activity of a subject's heart, and apply a second time-variable voltage to an output of a second sensing electrode;

measure artefacts arising from motion of the subject, and in a frequency domain, remove the measured artefacts from the first sensed signal or second sensed signal, wherein the removing comprises removing the first time-variable voltage from the second time-variable voltage output of the second sensing electrode in the frequency domain;

using a second displacement current sensor, comprising a second sensing electrode and a second guard electrode, wherein the second sensing electrode is configured to measure the first sensed signal or the second sensed signal dependent upon electrical activity of a subject's heart, wherein the first operational amplifier generates at its output to a second operational amplifier a current and a voltage at the first guard electrode, wherein the second operational amplifier receives at a negative virtual earth terminal a voltage from a second guard electrode of a second displacement current sensor, wherein the second operational amplifier generates at its output a voltage which is a motion artefact signal arising from motion of the subject's heart;

applying the current reference signal to the first guard electrode; sensing at the second guard electrode an additional signal dependent upon the first time-variable voltage;

measuring at least a part of variable impedance signal caused by relative motion impedance between the first guard electrode and the second guard electrode using at least the first time-variable voltage and the second time-variable voltage to identify a motion of the subject; and processing at least the first sensed signal or the second sensed signal applying the additional signal to compensate for the motion artefact signal for removing noise from the variable impedance signal and producing an electrical signal less affected by noise.

\* \* \* \* \*